United States Patent [19]

Baile et al.

[11] Patent Number: 5,389,664
[45] Date of Patent: Feb. 14, 1995

[54] ALLEVIATING STOMACH ULCERS IN SWINE

[75] Inventors: Clifton A. Baile, Chesterfield; Frances C. Buonomo, Glencoe; Carol L. McLaughlin, Chesterfield; Billy D. Vineyard, St. Louis, all of Mo.

[73] Assignee: Monsanto Company, St. Louis, Mo.

[21] Appl. No.: 223,377

[22] Filed: Apr. 5, 1994

Related U.S. Application Data

[63] Continuation of Ser. No. 910,863, Jul. 8, 1992, abandoned.

[51] Int. Cl.$^6$ .................. A61K 31/415; A61K 31/47; A61K 37/00; A61K 31/445
[52] U.S. Cl. ........................................ 514/394; 514/9; 514/11; 514/314; 514/338; 514/395; 514/396; 514/806; 514/866
[58] Field of Search ...................... 514/314, 338, 9, 11, 514/394, 395, 806, 866, 396

[56] References Cited

U.S. PATENT DOCUMENTS

| | | | |
|---|---|---|---|
| 4,045,563 | 8/1977 | Berntsson et al. | 424/263 |
| 4,045,564 | 8/1977 | Berntsson et al. | 424/263 |
| 4,182,766 | 1/1980 | Krasso et al. | 424/263 |
| 4,255,431 | 3/1981 | Junggren et al. | 424/263 |
| 4,359,465 | 11/1982 | Ruwart | 514/314 |
| 4,472,409 | 9/1984 | Senn-Bilfinger | 424/263 |
| 4,628,098 | 12/1986 | Nohara et al. | 546/271 |
| 4,689,333 | 8/1987 | Nohara et al. | 514/338 |
| 4,758,579 | 7/1988 | Kohl et al. | 514/338 |
| 4,861,868 | 8/1989 | Krivi | 530/399 |
| 4,873,337 | 10/1989 | Sih et al. | 546/271 |
| 5,013,743 | 5/1991 | Iwahi et al. | 514/338 |
| 5,039,806 | 8/1991 | Bradstraim et al. | 546/271 |
| 5,045,321 | 9/1991 | Makino et al. | 424/475 |
| 5,185,347 | 2/1993 | Katano et al. | 514/322 |
| 5,215,974 | 6/1993 | Alminger et al. | 514/80 |
| 5,223,515 | 6/1993 | Mikura et al. | 514/338 |

FOREIGN PATENT DOCUMENTS

0204215 12/1986 European Pat. Off. .
0302720 4/1987 European Pat. Off. .
1234058 6/1971 United Kingdom .

OTHER PUBLICATIONS

Adelstein et al. "Substituted Potential Inhibitors of H+/K+ ATPase" 31 J. Med. Chem. 1215-20 (1988).
Stapleton et al. "Sucralfate in the Prevention of Porcine Experimental Peptic Ulceration", Amer. J. Med. 21-22 (1989).
Smith and Kasson, J. Anim. Sci., vol. 68, No. 12, pp. 4019-4116 (1990).
Smith and Kasson J. Anim. Sci., vol. 69, No. 2, pp. 571-577 (1991).
Tksukimi et al., Gastroenterology, vol. 104, No. 4(2), 1992, p. A181.
Joseph Alper "Ulcers as an Infectious Disease", Science, vol. 260, pp. 159-160 (1993).
Silen, "Experimental Models of Gastric Ulceration and Injury", pp. G395-G402, American Physiol. Soc. (1988).
Glaven, S. B., and Sandor Szabo, "Experimetnal Gastric Mucosal Injury" The FASEB Journal, pp. 825-832 (1992).

Primary Examiner—Marianne M. Cintins
Assistant Examiner—K. Weddington
Attorney, Agent, or Firm—George R. Beck; Gary M. Pond

[57] ABSTRACT

Alleviation of stomach ulcers in swine which are being administered exogenous somatotropin, by administering to the swine a benzimidazole compound selected from heterocyclylalkyl(sulfinyl or thio)benzimidazoles and [benzimidazolyl(sulfinyl or thio)alkyl]anilines.

19 Claims, No Drawings

ALLEVIATING STOMACH ULCERS IN SWINE

This is a continuation of application Ser. No. 07/910,863, filed on Jul. 8, 1992, now abandoned.

In swine that are being administered a porcine somatotropin (PST), e.g., to increase their growth rate, feed-to-meat conversion efficiency, leanness and/or sow milk, the somatotropin may contribute to stomach ulcers which, in severe cases, can cause death. See Smith and Kasson, *J. Anim. Sci.* 68:4109–16 (1990) and 69:571–77 (1991). These authors indicate that the mechanism by which somatotropin causes such ulcers is unknown. The difficulty of understanding this mechanism has been increased by the failure of various commonly used anti-ulcer products to alleviate ulcers in swine to which a somatotropin is being administered.

For example, histamine $H_2$ receptor antagonists such as Tagamet® cimetidine (SmithKline Beecham), Zantac® ranitidine (Glaxo), Pepcid® famotidine (Merck) and Axid® nizatidine (Lilly) are widely used in treating stomach ulcers in humans. However, a histamine $H_2$ receptor antagonist (ranitidine) has been found to have little effect for alleviating ulcers in PST-treated swine when 150 mg/day of the ranitidine is administered by 3×daily injection for 7 days.

Also commonly used for ulcer treatment are cytoprotectants, such as those containing $Al(OH)_3$ and $Mg(OH)_2$, e.g., Carafate® sucralfate (Marion Merrell Dow), and De-Nol® colloidal bismuth subcitrate (Gist-Brocades). These form a complex with proteinaceous exudate (albumin) at the ulcer site and thus present a film barrier against diffusion of hydrogen ions to stomach epithelial tissue. However, the addition of 1 or 4 gm sucralfate/3 kg of a finely ground pelleted diet fed to PST-treated 58–67 kg swine has been ineffective or inconclusive for alleviating stomach ulcers, and the administration of 500 mg/day of De-Nol was likewise ineffective.

Various E-type prostaglandins have unequivocally demonstrated an ability to alleviate ulcers in humans. However, the synthetic prostaglandin $E_1$ methyl ester, Cytotec® misoprostol (Searle), has been found to have very little effect in alleviating ulcer development in PST-treated hogs using 2×daily oral gavages of misoprostal totaling either 400 or 800 μg/day. Free-radical scavengers have been found to alleviate stomach ulcers in hogs not being treated with PST. For example, Vitamin U has been found effective against diet-induced ulceration in hogs. Tamas, et al., *Oesophagogastric Ulcer in Swine and Vitamin U*, III-IV, 34 *Acta. Veterinaria Hungarica* 81–100 (1986). However, Vitamin U has been found not significantly effective against stomach ulcers in PST-treated hogs when included in feed at 800 ppm. Other free-radical scavengers, e.g., Vitamin E (100 IU/kg plus 0.25 ppm selenium), and other possible in-feed ulcer alleviators, e.g., wheat midds (5%), Santoquin® feed preservative (Monsanto) (0.75 gm/day), oat hulls (9%) and cysteine (800 ppm), have been found similarly ineffective or not statistically effective against stomach ulcers in PST-treated hogs.

Still other recognized stomach ulcer treatments have been found ineffective or not statistically effective in PST-treated hogs. For example, Vitamin K in the form of menadione (6 mg/day), a clotting time-associated drug, and alfalfa (9% in feed; high in Vitamins E and K) have been found ineffective, and feed additives that slow down the gastric emptying rate, such as tallow (6%) and Stafac® antibacterial growth promotant (0.011%) have been found ineffective or not statistically effective.

It is believed that at the rates of PST administration generally envisioned for commercialization, the proportion of swine that may die from the effects of PST-aggravated ulceration is rarely greater than a few percent and normally less than one percent. However, to more fully permit realization of the great potential of somatotropins for improving economics of the swine industry and providing higher quality (leaner) pork products, it is an object of this invention to provide methods and articles of manufacture useful for alleviating ulcers in swine being administered PST. Details of the practice and utility of this invention in achieving that objective and others will be apparent from the following disclosure.

SUMMARY OF THE INVENTION

This invention provides a method for alleviating ulcers, and decreasing concomitant mortality in swine which are being administered exogenous somatotropin, which comprises administering a benzimidazole compound selected from heterocyclylalkyl(sulfinyl or thio)benzimidazoles and [benzimidazolyl(sulfinyl or thio)alkyl]anilines to the swine in an amount effective to alleviate such ulcers and thereby improve the health and/or decrease mortality of the swine.

Also provided by the invention are articles of manufacture that are useful in practicing the method of this invention, which articles comprise a porcine somatotropin and a benzimidazole compound selected from heterocyclylalkyl(sulfinyl or thio)benzimidazoles and [benzimidazolyl(sulfinyl or thio)alkyl]anilines, said articles being adapted for contemporaneous injection of the somatotropin and benzimidazole compound to effect prolonged release into the circulatory system of the swine of somatotropin in an amount effective to increase the growth rate, feed efficiency, leanness or sow milk of the swine, and of the benzimidazole compound in an amount effective to alleviate stomach ulcers in the swine.

PRIOR ART

Heterocyclylalkyl(sulfinyl or thio)benzimidazoles are known to be useful for alleviating stomach ulcers in mammals that are not being administered exogenous somatotropin. See U.S. Pat. Nos. 4,045,563 and 4,045,564 (Berntsson, et al; issued Aug. 30, 1977); 4,182,766 (Krassó, et al., issued Jan. 8, 1980); 4,255,431 (Junggren, et al; issued Mar. 10, 1981); 4,472,409 (Senn-Bilfinger; issued Sep. 18, 1984); 4,628,098 (Nohara, et al; issued Dec. 9, 1986); 4,758,579 (Kohl, et al; issued Jul. 19, 1988); 4,873,337 (Sih, et al; issued Oct. 10, 1989); 5,039,806 (Brädström, et al; issued Aug. 13, 1991); and 5,045,321 (Makino, et al; issued Sep. 3, 1991), the disclosures of which are incorporated herein by reference. However, one of the most widely used compounds of that class, 5-methoxy-2-[(4-methoxy-3,5-dimethyl-2-pyridyl)methylsulfinyl]benzimidazole (Prilosec® omeprazole; Merck) has been found ineffective for alleviating swine stomach ulcers induced by bile duct ligation. Stapleton, et al., *Sucralfate in the Prevention of Porcine Experimental Peptic Ulceration*, 86 (Suppl. 6A) *Amer. J. Med.* 21–22 (1989). Various pyridylalkylthiobenzimidazoles, their oral or parenteral administration, and their biological (e.g., anti-inflammatory) activities are disclosed in British 1,234,058, which was published Jun. 3, 1971.

[Benzimidazolylsulfinylalkyl]anilines are also known to be useful for alleviating stomach ulcers in mammals that are not being administered exogenous somatotropin. See, e.g., Adelstein, et al., *Substituted 2-[(2-Benzimidazolysulfinyl)methyl]anilines as Potential Inhibitors of $H^+/K^+$ATPase*, 31 *J. Med. Chem.* 1215-20 (1988) and European Patent Appln. published Dec. 10, 1986 under No. 204,215, the disclosures of which are incorporated herein by reference.

DETAILED DESCRIPTION

This invention is useful with any swine to which a somatotropin is being administered. These swine may include sows to which the somatotropin is being administered to enhance milk production. However, the invention is most commonly used with growing swine (e.g., finishing hogs) which may be barrows, gilts or boars. These hogs usually have a body weight between about 20 and about 150 kg.

The somatotropins with which this invention is useful include any compound having somatotropin-like activity in swine. These include compounds equivalent to or otherwise providing biological activity approximating the effects of native porcine somatotropin. Examples are disclosed in U.S. Pat. Nos. 4,861,868 (Krivi; issued Aug. 29, 1989) and 5,104,806 (Souza; issued Apr. 14, 1992), European Patent Appln. published Feb. 28, 1990 under No. 355,460 (Cady, et al.), European Patent Appln. published Jun. 20, 1984 under No. 111,389 (Seeburg, et al.), European Patent Appln. published Apr. 4, 1984 under No. 104,920 (Movva, et al.) and European Patent Appln. published Jun. 5, 1991 under No. 429,788 (Wang, et al.), the disclosures of which are incorporated herein by reference. Administration of a growth hormone releasing factor or other somatotropin secretagogue that simulates administration of exogenous somatotropin by stimulating the release of additional endogenous somatotropin should be considered equivalent for purposes of this invention.

The PST can be administered by daily injection or other parenteral methods, and is desirably administered by injection or implantation of a delivery system from which the PST is released into the circulatory system of the swine for a period of at least about 1, and preferably at least about 3 weeks. A period of PST release for up to about 6 weeks, or even longer, is desirable. The administration may be at any rate (constant or variable) and in any amount effective to increase the growth rate, feed-to-meat conversion efficiency ("feed efficiency"), leanness or milk production of the swine. This is usually at an average rate of at least about 1, and preferably at least about 2 mg/day. For economic reasons and otherwise, the daily dose is usually not greater than about 20, more commonly not greater than about 10, and most desirably not greater than about 5 mg/day.

The benzimidazole compound used in this invention can be any heterocyclylalkyl(sulfinyl or thio)benzimidazole which is effective for alleviating stomach ulcers in swine, and especially those of the pars esophagea which, in swine, is particularly susceptible to gastric ulcers. Typically these benzimidazoles are effective for inhibiting $H^+/K^+$ATPase enzyme activity in parietal cells in swine stomachs.

As shown in the aforementioned prior art, the heterocyclyl radical in such benzimidazole compounds can be pyridyl, imidazolyl, imidazolinyl, benzimidazolyl, thiazolyl, thiazolinyl, quinolyl, or piperidyl, each of which can be further unsubstituted or have 1, 2 or 3 ring substituents (alike or different) which do not unacceptably interfere with performance of the benzimidazole compound for use in this invention. These substituents (alike or different) can be chosen from chloro, bromo, fluoro, iodo, alkyl and fluorinated alkyl groups, wherein each alkyl can be straight-chain or branched and contain one, two, three or four (preferably one) carbon atom(s).

Also as shown in that prior art, the alkyl radical linking the heterocyclyl radical and the sulfur atom in the sulfinyl or thio radical can be straight-chain or branched and can contain one, two, three or four (preferably one) carbon atom(s). Used illustratively herein are the following benzimidazoles:

timoprazole—2-[2-pyridylmethylsulfinyl]benzimidazole;

thio analog of timoprazole*—2-[2-pyridylmethylthio]benzimidazole;

omeprazole 5-methoxy-2-[(4-methoxy-3,5-dimethyl-2-pyridyl)methylsulfinyl]benzimidazole; and lansoprazole—2-[[3-methyl-4-( 2,2,2 trifluoroethoxy )-2-pyridyl) ]methylsulfinyl ]benzimidazole.

*sometimes referred to as timoprazole sulfide or reduced timoprazole.

Most preferred for use in this invention are the 2-[2-pyridylmethyl(sulfinyl or thio)]benzimidazoles, including especially timoprazole, its thio analog, and the 5-methoxy-2-[(4-methoxy-3,5-dimethyl-2-pyridyl)methylsulfinyl]benzimidazoles, including omeprazole. Normally, timoprazole provides excellent results and, especially in some modes of administration such as injection of pellets, its thio analog provides even better results, e.g., in terms of prolongation and steadiness of release from the injected pellet(s). Methods for preparing such benzimidazoles are well known; some are described in the patents and patent applications cited in the preceding description of prior art. Various 2-[2-pyridylmethylthio]benzimidazoles useful in this invention, their preparation and a method for their conversion to the corresponding 2-[2-pyridylmethylsulfinyl]benzimidazoles, also useful in this invention, are disclosed in European Patent Appln. published Aug. 3, 1988 under No. 302,720 and/or the aforementioned British Patent 1,234,058, the disclosures of which are incorporated herein by reference. Many similarly useful structural variations of these compounds and methods for their preparation will be apparent to those skilled in the art.

Alternatively, the benzimidazole compound used in this invention can be any [benzimidazolyl(sulfinyl or thio)alkyl]aniline which is effective for alleviating stomach ulcers in swine, and especially those of the pars esophagea. Typically these benzimidazoles are effective for inhibiting activity of the acid secretory enzyme $H^+/K^+$ATPase. Preferred among these benzimidazoles are 2-[(2-benzimidazolyl sulfinyl or thio)methyl]anilines which can be further unsubstituted or have additional substituents (alike or different) chosen from chloro, bromo, fluoro, iodo, alkyl and fluorinated alkyl groups, each containing 1, 2, 3 or 4 carbon atoms, provided such substituents do not unacceptably interfere with performance of the benzimidazole compound for use in this invention. Specific illustrations of these benzimidazoles compounds are:

2-[(2-benzimidazolylthio)methyl]-N-methylaniline;
2-[(2-benzimidazolylsulfinyl)methyl]-N-methylaniline;
2-[(2-benzimidazolylthio)methyl]-4-methylaniline; and
2-[(2-benzimidazolylsulfinyl)methyl]-4-methylaniline.

The benzimidazole compound can be administered orally, e.g., in feed or water, or parenterally, e.g., by injection together with or separately from the somatotropin. Desirably the somatotropin and benzimidazole are administered simultaneously or contemporaneously, i.e., by injecting or implanting doses of each from which they will be concurrently released into the circulatory system of the swine over a prolonged (preferably substantially similar) period of time. Such prolonged release may be accomplished from an implanted osmotic pump containing a flowable formulation of the benzimidazole compound, or injected pellet(s) made by compacting the dry particulate benzimidazole in a quantity enough to provide the required average daily dose for the desired length of time. The rate and amount of administration of the benzimidazole compound are those effective to significantly alleviate (i.e., prevent or reduce the severity of) stomach ulcers in the swine, particularly those of the pars esophagea. These will depend on the potency of the specific benzimidazole compound being employed, the ulcer susceptibility of the breed or other characteristics of the swine in the environment in which the swine are being treated and maintained. Although the rate and amount of administration can vary widely, they will most commonly be at least about 1 (preferably at least about 5) mg/day, and will usually be not greater than about 50 (preferably not greater than about 25 mg/day.

The following specific examples are illustrative only and do not imply any limitations on the scope of this invention.

EXAMPLES 1–4

Several benzimidazole compounds were tested as alleviators of stomach ulcers in swine being administered a PST. 60 cross-bred barrows weighing about 90–100 kg were randomly assigned to the following groups of 10 hogs each:

Group 1—Control (administered neither PST nor benzimidazole).
Groups 2 thru 6—Injected with a high dose (20 mg/day) of PST by daily injection for 6 days to aggravate ulcer development for this study of ulcer inhibition effects.
Group 3 (Example 1)—Additionally administered 40 mg/day omeprazole by single oral gavage.
Group 4 (Example 2)—Additionally administered 40 mg/day omeprazole by twice-daily oral gavage of 20 mg.
Group 5 (Example 3)—Additionally administered 40 mg/day timoprazole by twice-daily injection of 20 mg.
Group 6 (Example 4)—Additionally administered 400 mg/day timoprazole by twice-daily injection of 200 mg.

A PST having an N-alanyl linked to the natural PST sequence, as disclosed in U.S. Pat. No. 4,861,868, was employed. All hogs had finely ground, pelleted and reground feed (18% protein with 0.25% supplemental lysine) available ad libitum. After 6 days, stomachs from all hogs were recovered and scored for ulceration according to the following system.

Ulcer Scoring

Each stomach is removed by severing the esophagus and duodenum 5 cm away from their connections with the stomach. The stomach is cut from the pylorus along the greater curvature to within 5 cm of the esophageal opening. The stomach is emptied, its inner surface is gently cleaned without abrading the esophageal area, and the stomach is then spread open with its inner surface facing upward. The severity of any ulcer present is rated by evaluating together the size and depth of the lesion, as follows. A lesion which encompasses essentially all of the esophageal area of the stomach is designated total. If a substantial proportion of the area of epithelial tissue remains, the lesion is designated partial. The depth of the ulcer is designated mild, moderate or severe. Mild ulcers are those in which the surface epithelial layer is slightly reddened. An erosion with a depth of approximately 0.25 mm is designated moderate. A very deep erosion (e.g., several mm) which results in complete loss of the epithelial layer in the ulcerated area is designated severe. After the size (area) and depth of the ulcer are determined, the severity of the ulcer is scored numerically as follows:

| | |
|---|---|
| Partial and Mild - 1 | Total and Moderate - 7 |
| Total and Mild - 3 | Partial and Severe - 8 |
| Partial and Moderate - 5 | Total and Severe - 10 |

Results of the ulcer scoring for Groups 1–6 are in Table I:

TABLE I

| | Group 1 Control | Group 2 20 mg/d pST | 20 mg/d pST | | | |
|---|---|---|---|---|---|---|
| | | | Group 3 40 mg omeprazole once daily | Group 4 20 mg omeprazole twice daily | Group 5 40 mg timoprazole once daily | Group 6 400 mg timoprazole once daily |
| Number of Hogs | 10 | 10[1] | 10 | 10 | 10 | 10 |
| Ulcer Score | 0.10 | 8.00 | 2.40 | 1.60 | 0.50 | 0.00 |

[1] One hog died on day 5. The cause was undetermined. However, an ulcer was not present.

These results show that omeprazole and, to an even greater extent, timoprazole are highly effective for alleviating stomach ulcers in PST-treated swine.

Comparative Examples A & B

In the study which included Examples 1–4, 2 additional groups of 10 hogs, each being administered the same PST in the same manner and the same amount (20 mg/day), were administered during the same 6 day period either 150 mg/day of ranitidine (50 mg injected 3×daily) or 800 μg/day of misoprostol (400 μg 2×daily by oral gavage). Ulcer scores for these 2 groups were 4.90 and 6.67, respectively, indicating that neither treatment was substantially effective for alleviating stomach ulcers in the PST-treated swine.

EXAMPLES 5–7

Timoprazole was tested as an alleviator of stomach ulcers in swine being administered a PST as in Examples 1–4. Forty cross-bred barrows weighing about 90–100 kg were randomly assigned to the following 4 groups of 10 hogs each:

Group 1—Injected with a high dose (20 mg/day) of PST by daily injection for 6 days to aggravate ulcer development for this study of ulcer inhibition effects.

Group 2 (Example 5)—40 mg/day timoprazole by twice-daily injection of 20 mg.

Group 3 (Example 6)—10 mg/day timoprazole by twice-daily injection of 5 mg.

Group 4 (Example 7)—10 mg/day timoprazole by steady infusion from an implanted Alzet pump.

All hogs had finely ground, pelleted and reground feed (18% protein with 0.25% supplemental lysine) available at libitum. After 7 days, stomachs from all surviving hogs were scored for ulceration according to the system described in Examples 1–4, with the results shown in Table II.

TABLE II

| | 20 mg/d pST | | | |
|---|---|---|---|---|
| | Group 1 no timoprazole | Group 2 20 mg timoprazole twice daily | Group 3 5 mg timoprazole twice daily | Group 4 10 mg/d timoprazole (Alzet) |
| Number of Hogs | 10[1] | 10[1] | 10[1] | 10[1] |
| Ulcer Score | 7.80$^c$ | 1.10$^a$ | 2.70$^{ab}$ | 4.30$^b$ |

[1]One hog within each of the 4 treatments died within a 2-day period (days 3–4).

EXAMPLES 8–11

Several different administrations of timoprazole or its thio analog were tested for alleviation of stomach ulcers in swine being administered by daily injection a PST of the kind employed in Examples 1–4. 80 cross-bred barrows weighing about 90–100 kg were randomly assigned to the following 8 groups of 10 hogs each:

Group 1—Control (administered neither PST nor a benzimidazole).

Group 2—Injected for 28 days with 20 mg/day PST.

Group 3 (Example 8)—Injected with 20 mg PST/day and 40 mg timoprazole/day for 28 days.

Group 4 (Example 9)—Injected with 20 mg PST/day for 6 days and then, for 22 days, 20 mg PST/day and 40 mg timoprazole/day.

Group 5 (Example 10)—Injected with 20 mg PST/day for 6 days and then, for 22 days, 3 mg PST/day and 10 mg timoprazole/day.

Group 6—Injected with 20 mg PST/day for 6 days and then 3 mg PST/day for 22 days.

Group 7—Administered neither PST nor a benzimidazole for 22 days; then injected with 20 mg PST/day for 6 days.

Group 8 (Example 11)—Administered neither PST nor a benzimidazole for 22 days and then, for 6 days, 20 mg PST/day and 40 mg/day of 2-[2-pyridylmethylthio]benzimidazole.

All hogs had finely ground, pelleted and reground feed (18% protein with 0.25% supplemental lysine) available ad libitum. After 29 days, stomachs from all hogs (except as noted) were scored for ulceration according to the system used in Examples 1–4. Results are in Table III.

TABLE III

| | Group 1 | Group 2 | Group 3 | Group 4 | Group 5 | Group 6 | Group 7 | Group 8 |
|---|---|---|---|---|---|---|---|---|
| Number of Hogs | 10 | 10[1] | 10[2] | 10[3] | 10 | 10[4] | 10 | 10 |
| Ulcer Score | 0.1 | 6.1 | 0.9 | 1.0 | 0.1 | 0.6[5] | 6.7 | 1.1 |

[1]One hog died on each of days 10, 16 and 23.
[2]One hog died on day 12.
[3]One hog died on day 6.
[4]One hog died on day 3. This animal was not included in the ulcer score.
[5]There was evidence that severe ulcers over a very large portion of the esophageal area had healed, presumably during the final 22 days during which PST had been administered at the rate of only 3 mg/day.

These results show that timoprazole and its thio analog are highly effective for alleviating stomach ulcers in PST-treated swine.

While specific embodiments of the invention have been described, it will be apparent to those skilled in the art that various modifications thereof can be made without departing from the true spirit and scope of the invention. Accordingly, it is intended that the following claims cover all such modifications within the full inventive concept.

We claim:

1. A method for alleviating stomach ulcers in swine which comprises:

administering to swine a compound, effective to alleviate pars esophageal ulcers in swine being administered exogenous porcine somatotropin, in an amount which is effective to alleviate said ulcers, wherein said compound being a benzimidazole compound effective for inhibiting H+/K+ ATPase activity in parietal cells in swine stomachs which is selected from heterocyclylalkyl(sulfinyl or thio)benzimidazoles and [benzimidazolyl(sulfinyl or thio)alkyl]anilines.

2. A method of claim 1 in which the benzimidazole compound is a 2-[2-pyridylmethyl(sulfinyl or thio)]benzimidazole.

3. A method of claim 2 in which the benzimidazole compound is 2-[2-pyridylmethylthio]benzimidazole.

4. A method of claim 2 in which the benzimidazole compound is 2-[2-pyridylmethylsulfinyl]benzimidazole.

5. A method of claim 2 in which the benzimidazole compound is 5-methoxy-2-[(4-methoxy-3,5-dimethyl-2-pyridyl)methylsulfinyl]benzimidazole.

6. A method of claim 1 in which the benzimidazole compound is administered by injection contemporaneously with the somatotropin.

7. The method of claim 1 wherein:
the effective amount comprises an amount of the benzimidazole compound effective for releasing a daily dose between about 1 and about 50 milligrams per day.

8. The method of claim 7 wherein:
the daily dose comprises between about 5 and about 50 milligrams per day.

9. The method of claim 7 wherein:
the daily dose comprises between about 5 and about 25 milligrams per day.

10. The method of claim 1 wherein:
the exogenous somatotropin is being administered in an amount effective for aggravating ulcer development in the pars esophagea.

11. The method of claim 1 wherein:

the exogenous somatotropin is being administered at an average rate from about 1 to about 20 milligrams per day.

12. The method of claim 11 wherein:
the exogenous somatotropin is being administered at an average rate from about 1 to about 10 milligrams per day.

13. The method of claim 11 wherein:
the exogenous somatotropin is being administered at an average rate from about 1 to about 5 milligrams per day.

14. The method of claim 11 wherein:
the exogenous somatotropin is being administered at an average rate from about 2 to about 5 milligrams per day.

15. The method of claim 11 wherein:
the administered exogenous somatotropin is released in the swine for a period of at least 1 week.

16. The method of claim 11 wherein:
the administered exogenous somatotropin is released in the swine for a period of at least 3 weeks.

17. The method of claim 11 wherein:
the administered exogenous somatotropin is released in the swine for a period of more than 6 weeks.

18. The method of claim 1 wherein:
the exogenous somatotropin and the benzimidazole compound are concurrently released into the swine over a period of time.

19. The method of claim 18 wherein:
the period of time for release of each of the exogenous somatotropin and the benzimidazole compound is substantially similar.

* * * * *